United States Patent [19]

Kelman

[11] 4,268,921
[45] May 26, 1981

[54] INTRAOCULAR LENSES

[76] Inventor: Charles D. Kelman, 73 Bacon Rd., Old Westbury, N.Y. 11568

[21] Appl. No.: 86,804

[22] Filed: Oct. 22, 1979

[51] Int. Cl.³ ............................ A61F 1/16; A61F 1/24
[52] U.S. Cl. ......................................................... 3/13
[58] Field of Search ........................................ 3/13, 1

[56]   References Cited

U.S. PATENT DOCUMENTS

| 4,056,855 | 11/1977 | Kelman | 3/13 |
| 4,092,743 | 6/1978 | Kelman | 3/13 |
| 4,134,161 | 1/1979 | Bayers | 3/13 |

OTHER PUBLICATIONS

Covered Bridge an Update on Lens Implantation by John H. Sheets, M.D. or Bridge Over Troubled Waters (Book), (3rd Attempt), 1977, pp. 5–13.

*Primary Examiner*—Ronald L. Frinks
*Attorney, Agent, or Firm*—Philip Rodman

[57]   ABSTRACT

A multi-piece intraocular lens includes a medial light-focusing lens body and a plurality of position fixation members for holding the lens body in proper position in the eye. At least one of the position fixation members is separate from and attachable to the lens body. The separate position fixation member is assembled to the lens body after both it and the lens body have been separately inserted into the eye.

26 Claims, 4 Drawing Figures

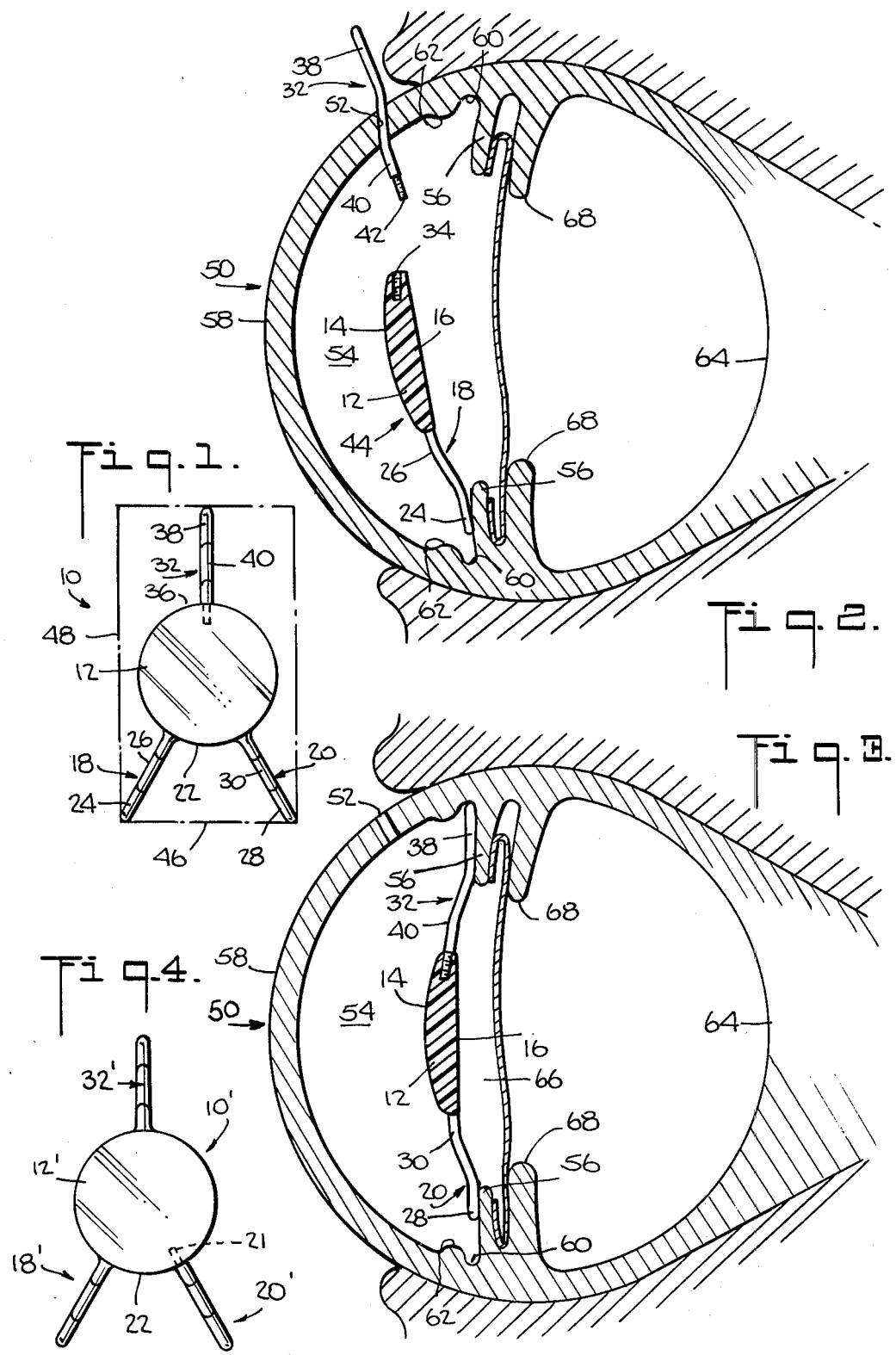

INTRAOCULAR LENSES

This invention relates to intraocular lenses for the human eye and, more particularly, to a multi-piece intraocular lens that is assembled after insertion in the eye.

The lens of an eye is known as a cataract when it becomes partially or totally opaque and obstructs the passage of light, thereby impairing vision. A cataract condition is irreversible and the affected lens is usually removed if vision is to be restored.

Substituted artificial lenses provided after cataract removal, such as spectacles, contact lenses or intraocular lenses enable the eye to restore a focused image on the retina. The intraocular lens, which is implanted permanently in the eye, has become increasingly popular because it requires no day-to-day maintenance and is not visibly apparent to other individuals.

An intraocular lens generally includes a light-focusing lens body and a support structure to stabilize the position of the lens body in the eye. The term "implantation" as used herein refers to the stabilized position of the intraocular lens in the eye and the term "intraocular lens" is intended to include the lens body and its associated support structure.

A corneo-scleral incision is often used for insertion of the intraocular lens in the eye. The term "insertion", as used herein, refers to the passage of the intraocular lens into the eye. The size of the corneo-scleral incision is based upon, among other factors, the overall size of the intraocular lens. Since the rate of healing following a lens implantation is affected by the size of the corneo-scleral incision, it is desirable to minimize the size of the required incision, as by utilizing an intraocular lens that can be snaked through an incision such as disclosed in my U.S. Pat. No. 4,092,743.

Among the several objects of the present invention may be noted the provision of an intraocular lens having a removable support member, a multi-piece intraocular lens that is assembled after insertion in the eye and an intraocular lens having a lens body with a support structure of greater peripheral extent than the lens body but insertable in an incision the size of which is based upon the size of just the lens body alone, without a support structure.

Other objects and features will be in part apparent and in part pointed out hereinafter.

The present invention relates to a novel multi-piece intraocular lens that is assembled in the eye after separate insertion of the components.

In accordance with the invention, the intraocular lens comprises a medial light-focusing lens body having first and second position fixation means at first and second opposite peripheral sections of the lens body corresponding to upper and lower circumferential groove portions of the eye. One of the position fixation means includes a first support member joined to one of the peripheral sections of the lens body. The other position fixation means includes second and third support members both joined to separate portions of the other peripheral section of the lens body. The first and second peripheral sections in effect define separate first, second and third peripheral portions which are joined to a respective first, second and third support member. In a preferred form of the invention at least one of the first, second and third support members or position fixation members is formed separately of the lens body and attachable thereto.

In one embodiment of the invention, the second and third support members are integrally joined to a generally circular lens body and extend radially therefrom at a predetermined angle with respect to each other. Free end portions of the integrally joined support members are spaced apart a distance that is greater than the diameter of the lens body.

The first support member is formed separately of the lens body and includes one end portion that engages a recess in the lens body. The first support member is held in the recess by detent means defined, for example, by a threaded engagement or a press-fitting engagement of the support member in the recess. An opposite free end portion of the first support member is spaced from the free end portions of the second and third support members by a distance that is also greater than the diameter of the lens body.

In another embodiment of the invention the first support member is integrally joined to the lens body and one of the second and third support members is formed separately of the lens body and attachable thereto. The other of the second and third support members is also integrally joined to the lens body.

The lens body and its integrally joined support members are inserted in the eye through a corneo-scleral incision, for example. Thereafter the separately formed support member is inserted in the eye through the corneo-scleral incision and assembled to the lens body. Assembly of the intraocular lens in the eye after separate insertion of the individual components permits use of an eye incision that is the minimum size necessary to accomodate a similar size lens body without support structure. It is also feasible to use a relatively small second incision alongside the corneo-scleral incision for insertion of the separate support member.

The invention accordingly comprises the constructions hereinafter described, the scope of the invention being indicated in the following claims.

In the accompanying drawing, in which various embodiments of the invention are illustrated, FIG. 1 is a simplified plan view of an intraocular insert incorporating one embodiment of the present invention;

FIG. 2 shows the separate components of the intraocular insert during insertion in the eyeball;

FIG. 3 is a simplified schematic sectional view of an eyeball with the assembled intraocular insert in its implanted position; and, FIG. 4 is another embodiment of the invention.

Corresponding reference numbers indicate corresponding parts throughout the several views of the drawing.

Referring now to the drawing, an intraocular insert incorporating one embodiment of the invention is generally indicated by reference number 10 in FIG. 1.

The intraocular insert includes a medial light-focusing lens body 12 having a convex or flat anterior surface 14 and a generally flat or convex posterior surface 16. Position fixation means comprising a pair of support members 18 and 20 are integrally joined to separate portions of a peripheral section 22 of the lens body 12.

The support member 18, which has a generally round, oval or rectangular cross-sectional shape, includes a seating portion 24 offset from a main portion 26. The support member 20, which is similar in structure to the support member 18, includes a seating portion 28 and a main portion 30.

The distance between the seating portions 24 and 28 exceeds the diameter of the lens body 12 as shown in FIG. 1. The lens body 12 and the support members 18 and 20 are formed of any suitable material which is compatible with the environment at the interior of the eyeball, such as a non-toxic plastic, for example, polymethylmethacrylate.

The intraocular insert 10 includes additional position fixation means comprising a support member 32 of generally round, oval or rectangular cross-sectional shape formed separately of the lens body 12. The support member 32, which is engageable in a recess 34 formed at a peripheral section 36 of the lens body, has a seating portion 38 offset from a main portion 40 and can be formed of any suitable inert material such as plastic, as previously described, or for example, platinum. Detent means for maintaining engagement of the support member 32 with the lens body 12 comprise an external thread formed at a free end 42 of the support member 32 (FIG. 2) and an internal thread formed in the lens recess 34.

Referring to FIG. 2, the lens body 12 with the integrally joined support members 18 and 20, hereinafter referred to as the lens component 44, is inserted in an eyeball 50 using suitable known medical procedures which include, for example, a corneo-scleral incision 52. Insertion of the lens component 44 is preferably accomplished by orienting the lens body 12 so that one and only one of the support members 18 or 20 enters the incision 52 before insertion of the other support member.

For example, the support member 18 first enters the incision 52 followed by the lens body 12 which is rotated through an arc that will permit positioning of the support member 20 as the last element of the lens component 44 to be passed through the incision. This is a snaking-in of the insert in a manner similar to that described in my U.S. Pat. No. 4,092,743.

It will be noted from FIG. 1 that the distance between the seating portions 24 and 28 of the support members 18 and 20 defines a first dimensional side 46 of a rectangle shown in dotted outline in FIG. 1. The distance from a line joining the seating portions 24, 28 to the seating portion 38 of the support member 32 defines a second dimensional side 48 of the rectangle. The rectangle, which encloses the entire structure of the intraocular insert 10, does not contact any portion of the periphery of the lens body 12.

However, in accordance with the intraocular insertion procedure described and referred to above, the entire lens component 44 (FIG. 2) can be inserted in an incision 52 having a size that corresponds to that of the lens body 12 even though the distance between the support member seating portions 24 and 28 exceeds the diameter of the lens body 12. Thus, the corneo-scleral incision 52 is substantially the same size as would be necessary for insertion of the lens body 12 alone, minus any support members.

After the lens component 44 has been inserted into the eyeball 50 as shown in FIG. 2, the attachable support member 32 is passed through the incision 52. The inserted support member 32 is then assembled to the lens component 44 in the eyeball 50 by engaging the threaded end portion 42 with the threaded recess 34.

The assembled intraocular insert 10 is implanted in the anterior chamber 54 of the eyeball 50 between the iris 56 and the cornea 58 as shown in FIG. 3. The implantation is stabilized by locating the seating portions 24 and 28 of the support members 18 and 20 in the lower portion of an annular groove 60 (FIG. 2) defined between the scleral spur 62 and the iris 56, and the seating portion 38 of the support member 32 in an upper portion of the annular groove 60. Thus the peripheral section 36 of the lens body corresponds to the upper portion of the annular groove 60 and the peripheral section 22 of the lens body corresponds to the lower portion of the annular groove 60. In this manner the implanted intraocular lens 10 aligns the lens body 12 with the pupil 66 of the eye to permit the eye to restore a focused image on the retina 64.

As will be apparent to those skilled in the art, the intraocular insert 10 can be implanted at other locations in the eye such as in the posterior chamber defined between the iris 56 and the posterior capsule and ciliary body 68 of the eye. The dimensions of the intraocular insert 10 can vary and eyeball measurements that are usually made before surgery will determine the precise dimensions of the intraocular insert for each patient.

Nevertheless, to exemplify the magnitudes being dealt with, the overall height 48 of the intraocular insert 10 from the free end of seating portions 24 or 28 to the free end of the seating portion 38 is approximately 12 mm., the diameter of the lens body 12 is approximately 4 mm., the maximum thickness of the lens body 12 is approximately 0.4 mm., the angle between the support members 18 and 20 is approximately 60°, the distance 46 between the free end of the seating portions 24 and 28 is approximately 7 mm., the cross sectional width of the support members is approximately 1.2 mm., the cross sectional thickness of the support members is approximately 0.2 mm., the diameter of the recess 34 is approximately 0.2 mm., the depth of the recess 34 is approximately 1.5 mm., the thread size of the recess 34 is of any suitable precision thread size, and the offset between the main portions and the seating portions of the support members is approximately 0.7 mm.

It should be noted that the shape of the lens body 12 need not be circular but can be of elliptical or other suitable shape. The offset between the respective main portions 26, 30 and 40, and the respective seating portions 24, 28 and 38 of the respective support members 18, 20, and 32 helps maintain the lens body 12 out of contact with the iris 56. If desired, one or more of the support member seating portions 24, 28 and 38 can be secured to the iris using suturing procedures referred to in U.S. Pat. No. 4,092,743 or any other suitable known affixation techniques. Moreover, the attachable support member can be affixed to the lens body 12 using such joining techniques as press-fitting the free end 42 into an appropriately sized recess 34 or suturing the free end 42 to the lens body periphery 36.

Another embodiment of the intraocular insert, illustrated in FIG. 4 is generally indicated by the reference number 10'. The intraocular insert 10' differs from the intraocular insert 10 by virtue of the support member 20', corresponding to the support member 20, being formed separately of and detached from the lens body 12' and by virtue of the support member 32', corresponding to the support member 32, being integrally joined to the lens body 12'. Other structural details of the intraocular insert 10' substantially correspond with the intraocular insert 10. Thus the support member 20' is detented in the lens body 12' by means of, for example, a threaded end portion 21 engageable with a complementary threaded recess formed in the lens body 12'.

The procedure for inserting the intraocular insert 10' into an eye is similar to the insertion procedure described for the intraocular insert 10. For example, the lens body 12', with the integrally joined support members 18' and 32' is inserted in an eyeball through a corneo-scleral incision similar to that described for the intraocular insert 10. Once the lens body 12', with the integrally joined support members 18' and 32', is inserted in the eye it is oriented to permit insertion and attachment of the support member 20'.

Another alternative is to insert the support member 20' into the eye through a separate relatively small incision (not shown) made alongside the corneo-scleral incision through which the lens body 12' and integrally joined support members 18' and 32' are inserted. This alternative can also be used with the intraocular insert 10 of FIG. 1, whereby the support member 32 is insertable into the eye through a separate relatively small incision (not shown) made alongside the corneo-scleral incision 52.

Some advantages of the present invention evident from the foregoing description include an intraocular lens insert which can be passed through a corneo-scleral incision that is the minimum size necessary to accomodate the lens body above, an intraocular insert having support members that can be sequentially inserted into a corneo-scleral incision and a multi-piece intraocular lens insert that can be assembled after separate insertion of a lens component and support member in the eye.

In view of the above, it will be seen that the several objects of the invention are achieved and other advantageous results attained.

As various changes can be made in the above constructions without departing from the scope of the invention, it is intended that all matter contained in the above description or shown in the accompanying drawing should be interpreted as illustrative and not in a limiting sense.

What is claimed is:

1. An intraocular insert suitable for use as an artificial lens in the interior of a human eye, said eye interior having a groove extending circumferentially at upper and lower portions of the eye when viewed in cross-section, said upper and lower groove portions having respective interior peripheral surfaces, said insert comprising a medial light-focusing lens body with first and second opposite peripheral sections corresponding to said upper and lower groove portions, first position fixation means joined to said first peripheral section of said lens body and extending generally radially beyond said first peripheral section, said first position fixation means having a pair of spaced first seating portions engageable with one of said groove portions, second position fixation means being joined to said second peripheral section and extending generally radially beyond said second peripheral section, said second position fixation means having a second seating portion engageable with the other said groove portion such that the engagement of the first and second position fixation means with respective said groove portions align the lens body with respect to the pupil of the eye, one of said position fixation means being formed separately of and detached from the lens body and engageable with one of said peripheral sections for connection to said lens body when said insert is inserted into said eye and wherein said second position fixation means is formed separately of said lens body and comprises one end portion engageable with said one peripheral section and an opposite end portion defining said second seating portion and wherein an opening is formed in said one peripheral section of said lens body and said one end portion of said second position fixation means is of predetermined size and shape to permit disposition of said one end portion into said opening, and detent means provided with said opening and said one end portion for maintaining said disposition.

2. An intraocular insert as claimed in claim 1 wherein said first position fixation means comprise first and second support members extending outwardly of said lens body at a predetermined angle with respect to each other, said first and second support members having end portions respectively defining said pair of spaced first seating portions.

3. An intraocular insert as claimed in claim 1 wherein said opening is threaded and said one end portion of said second position fixation means is threadable in said threaded opening to constitute said detent means.

4. An intraocular insert as claimed in claim 1 wherein said opening and said one end portion of said second position fixation means are of complementary size and shape to permit a press-fitting of said one end portion into said opening to constitute said detent means.

5. An intraocular insert as claimed in claim 1 wherein the distance between the seating portions of said first position fixation means defines one dimensional side of a rectangle, and the distance from a line joining the seating portions of said first position fixation means to the seating portion of said second position fixation means defines a second dimensional side of said rectangle such that said rectangle is inscribable around the seating portions of said first position fixation means and the seating portion of the second position fixation means, the magnitude of said lens body being dimensionally smaller than the first and second dimensional sides of said rectangle such that said rectangle completely encloses said lens body without touching any portion of the periphery of said lens body.

6. A kit for an intraocular insert suitable for use as an artificial lens in the interior of a human eye, said eye interior having a groove extending circumferentially at upper and lower portions of the eye when viewed in cross-section, said upper and lower groove portions having respective interior peripheral surfaces, said kit including a medial light-focusing lens body with first and second opposite peripheral sections corresponding to said upper and lower groove portions, first and second position fixation members integrally joined to one of said peripheral sections and respectively extending generally radially beyond said one peripheral section at a predetermined angle with respect to each other, said first and second position fixation members respectively having first and second free outer seating end portions engageable with one of the groove portions upon implantation of said insert in said eye, and a recess formed in said lens body at said other peripheral section, said kit further including a third position fixation member separate from said lens body and having one end portion of complementary size and shape with said recess to permit disposition of said one end portion in said recess, detent means provided with said recess and said one end portion for maintaining said disposition, said third position fixation member including an opposite free outer seating end portion engageable with said other groove portion after said disposition such that the engagement of the first and second position fixation members with said one groove portion and the engagement of the third position fixation member with said other groove portion aligns the lens body with respect to the pupil of the eye.

7. A kit as claimed in claim 6 wherein the distance between the seating end portions of said first and second position fixation members defines one dimensional side of a rectangle, and the distance from a line joining the seating end portions of said first and second position fixation members to the seating portion of said third position fixation member defines a second dimensional side of said rectangle such that said rectangle is inscribable around the seating end portions of said first, said second and said third position fixation members, the magnitude of said lens body being dimensionally smaller than the first and second dimensional sides of said rectangle such that said rectangle completely encloses said lens body without touching any portion of the periphery of said lens body.

8. An intraocular insert as claimed in claim 6 wherein said recess is threaded and said one end portion of said third position fixation member is threadable in said threaded recess to constitute said detent means.

9. An intraocular insert as claimed in claim 6 wherein said recess and said one end portion of said third position fixation member are of complementary size and shape to permit a press-fitting of said one end portion into said recess to constitute said detent means.

10. An intraocular insert suitable for use as an artifical lens in the interior of a human eye, said eye interior having a groove extending circumferentially at upper and lower portions of the eye when viewed in cross-section, said upper and lower groove portions having respective interior peripheral surfaces, said insert comprising a medial light-focusing lens body with first, second and third peripheral portions, a first support member having a first seating portion engageable with one of said groove portions and being joined to one of said peripheral portions of said lens body and extending generally radially beyond said one peripheral portion, second and third support members respectively having second and third seating portions engageable with the other said groove portion and being respectively joined to the second and third peripheral portions of said lens body and respectively extending generally radially beyond said second and third peripheral portions, one of said support members being formed separately of the lens body and engageable with its corresponding peripheral portion to affix said one support member to said lens body, said other support members being integrally joined to said lens body at their corresponding peripheral portions such that the engagement of the first, second and third seating portions with their respective said groove portions align the lens body with respect to the pupil of the eye and wherein a threaded recess is formed in the peripheral portion of said lens body corresponding to said one support member, and said one support member has one end portion threadable in said threaded recess.

11. An intraocular insert as claimed in claim 10 wherein said first support member is formed separately of said lens body.

12. An intraocular insert as claimed in claim 10 wherein one of said second and third support members is formed separately of said lens body.

13. An intraocular insert as claimed in claim 10 wherein said first, second and third support members have end portions respectively defining said first, said second and said third seating portions and the distance between the end portions of said second and said third support members define one dimensional side of a rectangle, and the distance from a line joining the end portions of said second and said third support members to the end portion of said first support member defines a second dimensional side of said rectangle such that said rectangle is inscribable around the end portions of said first, said second and said third support members, the magnitude of said lens body being dimensionally smaller than the first and second dimensional sides of said rectangle such that said rectangle completely encloses said lens body without touching any portion of the periphery of said lens body.

14. An intraocular insert suitable for use as an artifical lens in the interior of a human eye, said eye interior having a groove extending circumferentially at upper and lower portions of the eye when viewed in cross-section, said upper and lower groove portions having respective interior peripheral surfaces, said insert comprising a medial light-focusing lens body with first, second and third peripheral portions, a first support member having a first seating portion engageable with one of said groove portions and being joined to one of said peripheral portions of said lens body and extending generally radially beyond said one peripheral portion, second and third support members respectively having second and third seating portions engageable with the other said groove portion and being respectively joined to the second and third peripheral portions of said lens body and respectively extending generally radially beyond said second and third peripheral portions, one of said support members being formed separately of the lens body and engageable with its corresponding peripheral portion to affix said one support member to said lens body, said other support members being integrally joined to said lens body at their corresponding peripheral portions such that the engagement of the first, second and third seating portions with their respective said groove portions align the lens body with respect to the pupil of the eye and wherein an opening is formed in the peripheral portion of said lens body corresponding to said one support member, and said one support member has one end portion of complementary size and shape with said opening to permit a press-fitting of said one end portion into said opening.

15. An intraocular insert as claimed in claim 14 wherein said first support member is formed separately of said lens body.

16. An intraocular insert as claimed in claim 14 wherein one of said second and third support members is formed separately of said lens body.

17. An intraocular insert as claimed in claim 14 wherein said first, second and third support members have end portions respectively defining said first, said second and said third seating portions and the distance between the end portions of said second and said third support members define one dimensional side of a rectangle, and the distance from a line joining the end portions of said second and said third support members to the end portion of said first support member defines a second dimensional side of said rectangle such that said rectangle is inscribable around the end portions of said first, said second and said third support members, the magnitude of said lens body being dimensionally smaller than the first and second dimensional sides of said rectangle such that said rectangle completely encloses said lens body without touching any portion of the periphery of said lens body.

18. An intraocular insert suitable for use as an artificial lens in the interior of a human eye, said eye interior having a groove extending circumferentially at upper and lower portions of the eye when viewed in cross-section, said upper and lower groove portions having respective interior peripheral surfaces, said insert comprising a medial light-focusing lens body with first, second and third peripheral portions, a first support member having a first seating portion engageable with one of said groove portions and being joined to one of said peripheral portions of said lens body and extending generally radially beyond said one peripheral portion, second and third support members respectively having second and third seating portions engageable with the other said groove portion and being respectively joined to the second and third peripheral portions of said lens body and respectively extending generally radially beyond said second and third peripheral portions, one of said support members being formed separately of the lens body and engageable with its corresponding peripheral portion to affix said one support member to said lens body, said other support members being integrally joined to said lens body at their corresponding peripheral portions such that the engagement of the first, second and third seating portions with their respective said groove portions align the lens body with respect to the pupil of the eye and wherein an opening is formed in the peripheral portion of said lens body corresponding to said one support member, and said one support member has one end portion of predetermined size and shape to permit disposition of said one end portion into said opening, and detent means associated with said opening and said one end portion for maintaining said disposition.

19. An intraocular insert as claimed in claim 18 wherein said first support member is formed separately of said lens body.

20. An intraocular insert as claimed in claim 18 wherein one of said second and third support members is formed separately of said lens body.

21. An intraocular insert as claimed in claim 18 wherein said first, second and third support members have end portions respectively defining said first, said second and said third seating portions and the distance between the end portions of said second and said third support members define one dimensional side of a rectangle, and the distance from a line joining the end portions of said second and said third support members to the end portion of said first support member defines a second dimensional side of said rectangle such that said rectangle is inscribable around the end portions of said first, said second and said third support members, the magnitude of said lens body being dimensionally smaller than the first and second dimensional sides of said rectangle such that said rectangle completely encloses said lens body without touching any portion of the periphery of said lens body.

22. A kit for an intraocular insert suitable for use as an artificial lens in the interior of a human eye, said eye interior having a groove extending circumferentially at upper and lower portions of the eye when viewed in cross-section, said upper and lower groove portions having respective interior peripheral surfaces, said kit including a medial light-focusing lens body with first and second opposite peripheral sections corresponding to said upper and lower groove portions, first and second position fixation members joined to respective said peripheral sections of said lens body and respectively extending generally radially beyond said respective peripheral sections at a predetermined angle with respect to each other, said first and second position fixation members respectively having first and second free outer seating end portions engageable with respective said groove portions upon implantation of said insert in said eye, and a recess formed in said lens body at one of said peripheral sections, said kit including a third position fixation member separate from said lens body and having one end portion of complementary size and shape with said recess to permit disposition of said one end portion in said recess, detent means associated with said recess and said one end portion for maintaining said disposition, said third position fixation member including an opposite free outer seating end portion engageable with one of said groove portions after said disposition such that two of said position fixation members are both situated at one of said peripheral sections and the remaining position fixation member is situated at the other said peripheral section, whereby the engagement of said first, said second and said third position fixation member with said upper and lower groove portions align the lens body with respect to the pupil of the eye.

23. A kit as claimed in claim 22 wherein the distance between the seating end portions of two position fixation members situated at one of said peripheral sections defines one dimensional side of a rectangle, and the distance from a line joining the end portions of the both situated position fixation members to the seating portion of said remaining position fixation member defines a second dimensional side of said rectangle such that the rectangle is inscribable around the end portions of said first, said second and said third position fixation members, the magnitude of said lens being dimensionally smaller than the first and second dimensional sides of said rectangle such that said rectangle completely encloses said lens body without touching any portion of the periphery of said lens body.

24. An intraocular insert as claimed in claim 22 wherein said recess is threaded and said one end portion of said third position fixation member is threadable in said threaded recess to constitute said detent means.

25. An intraocular insert as claimed in claim 22 wherein said recess and said one end portion of said third position fixation member are of complementary size and shape to permit a press-fitting of said one end portion into said recess to constitute said detent means.

26. An intraocular insert suitable for use as an artificial lens in the interior of a human eye, said eye interior having a groove extending circumferentially at upper and lower portions of the eye when viewed in cross-section, said upper and lower groove portions having respective interior peripheral surfaces, said insert comprising a medial light-focusing lens body with first and second opposite peripheral sections corresponding to said upper and lower groove portions, first position fixation means comprising a first support member joined to said first peripheral section of said lens body and extending generally radially beyond said first peripheral section to define a first seating portion engageable with one of said groove portions, second position fixation means comprising independent second and third members joined to said second peripheral section of said lens body said second and said third support members extending radially beyond said second peripheral section at a predetermined angle with respect to each other to define respective second and third seating portions engageable with the other said groove portion such that the engagement of the first and second position fixation means with respective said groove portions align the lens body with respect to the pupil of the eye, at least one of said second and said third support members being formed separately of and detached from said lens body for connection to said lens body when said insert is inserted into said eye and means for connecting said one of said second and said third support members to said lens body.

* * * * *